United States Patent
Chan

(10) Patent No.: US 8,608,668 B2
(45) Date of Patent: *Dec. 17, 2013

(54) LANCET PROTECTIVE CAP

(75) Inventor: Frank A. Chan, Sunnyvale, CA (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 105 days.

This patent is subject to a terminal disclaimer.

(21) Appl. No.: 13/182,558

(22) Filed: Jul. 14, 2011

(65) Prior Publication Data

US 2011/0270130 A1    Nov. 3, 2011

Related U.S. Application Data

(60) Continuation of application No. 12/355,976, filed on Jan. 19, 2009, now Pat. No. 8,062,233, which is a division of application No. 11/052,610, filed on Feb. 7, 2005, now Pat. No. 7,479,118.

(51) Int. Cl.
   *A61B 5/00*           (2006.01)
   *A61B 17/14*        (2006.01)
   *A61B 17/32*        (2006.01)

(52) U.S. Cl.
   USPC .......................................... 600/583; 606/181

(58) Field of Classification Search
   USPC .................... 600/583; 206/363, 438; 606/181
   See application file for complete search history.

(56) References Cited

U.S. PATENT DOCUMENTS

| | | | |
|---|---|---|---|
| 2,866,542 A | 12/1958 | Svirchev | |
| 2,998,880 A | 9/1961 | Ladd | |
| 3,669,256 A | 6/1972 | Jacob | |
| 3,910,455 A | 10/1975 | Ferraro | |
| 4,123,840 A | 11/1978 | Rumer, Jr. | |
| 4,637,403 A | 1/1987 | Garcia et al. | |
| 4,915,697 A | 4/1990 | DuPont | |
| 5,163,442 A | 11/1992 | Ono | |
| 5,409,133 A | 4/1995 | Gringer | |
| 5,474,179 A * | 12/1995 | Iosif et al. | 206/363 |
| 5,795,632 A | 8/1998 | Buchalter | |
| 6,010,519 A | 1/2000 | Mawhirt et al. | |
| 6,051,293 A | 4/2000 | Weilandt | |
| 6,315,738 B1 | 11/2001 | Nishikawa et al. | |
| 6,349,229 B1 | 2/2002 | Watanabe et al. | |

(Continued)

FOREIGN PATENT DOCUMENTS

| | | |
|---|---|---|
| GB | 2 084 005 A | 4/1982 |
| WO | WO2004/060174 | 7/2004 |
| WO | WO2004/086970 | 10/2004 |

OTHER PUBLICATIONS

European Patent Application No. 06 723 003.7 Written Opinion mailed May 25, 2009.

*Primary Examiner* — Brian Szmal
*Assistant Examiner* — Megan Leedy
(74) *Attorney, Agent, or Firm* — Woodard, Emhardt, Moriarty, McNett & Henry LLP

(57) ABSTRACT

A unique technique for maintaining the sterility and integrity of a lancet tip. One or more lancet tips are sandwiched between a first web and a second web of material to protect the sterility of the lancet tips. The first and second webs are heat fused together to form a structure that covers and encapsulates the lancet tips to protect the integrity of the lancet tips. The structure is cut to form individual protective caps to detachably cover each of the lancet tips.

19 Claims, 5 Drawing Sheets

(56) References Cited

U.S. PATENT DOCUMENTS

| | | |
|---|---|---|
| 6,808,691 B1 | 10/2004 | Herve et al. |
| 7,223,248 B2 | 5/2007 | Erickson et al. |
| 2002/0168290 A1 | 11/2002 | Yuzhakov et al. |
| 2002/0177761 A1 | 11/2002 | Orloff et al. |
| 2003/0050573 A1 | 3/2003 | Kuhr et al. |
| 2003/0143113 A2 | 7/2003 | Yuzhakov et al. |
| 2003/0144608 A1 | 7/2003 | Kojima et al. |
| 2003/0199894 A1 | 10/2003 | Boecker et al. |
| 2004/0064068 A1 | 4/2004 | DeNuzzio et al. |
| 2004/0127929 A1 | 7/2004 | Roe |
| 2004/0163987 A1 | 8/2004 | Allen |
| 2005/0019212 A1 | 1/2005 | Bhullar et al. |
| 2005/0021066 A1 | 1/2005 | Kuhr et al. |
| 2005/0036909 A1 | 2/2005 | Erickson et al. |
| 2005/0245954 A1 | 11/2005 | Roe et al. |
| 2005/0277850 A1 | 12/2005 | Mace et al. |
| 2006/0079810 A1 | 4/2006 | Patel et al. |
| 2006/0195128 A1 | 8/2006 | Alden et al. |
| 2009/0043325 A1 | 2/2009 | Fritz et al. |

\* cited by examiner

LANCET PROTECTIVE CAP

CROSS REFERENCE TO RELATED APPLICATION

This application is a continuation of U.S. application Ser. No. 12/355,976, filed Jan. 19, 2009, now U.S. Pat. No. 8,062,233 which is a divisional of U.S. application Ser. No. 11/052,610, filed Feb. 7, 2005, now U.S. Pat. No. 7,479,118, which are hereby incorporated by reference.

BACKGROUND OF THE INVENTION

The present invention generally relates to a unique technique for maintaining sterility and integrity of a lancet tip. More specifically, but not exclusively, the present invention concerns a manufacturing technique for quickly and easily producing a plurality of protective caps. Moreover, a plurality of lancet tips with protective caps can be stored in a cartridge or cassette.

Body fluid sampling devices have been developed to draw body fluid, such as blood or interstitial fluid, from a person and analyze the drawn fluid for any number of characteristics, such as blood glucose levels for diabetics. To monitor a patient's condition, a medical practitioner or the individual first creates an incision in the skin by lancing the subject's skin with a lancet. To avoid infection of the incision site and/or contamination of the fluid collected, the lancet is sterilized and packaged in a sterile manner prior to use. One form of packaging the lancet in a sterile environment is to place an entire lancet between two walls of a layered material and heat seal a portion of the layered material around the entire lancet. The inner layers of the walls are usually formed from a protective sterilized padding and the outer layers of the walls are usually formed of a foil material. Between the inner walls and the outer walls is an intermediate layer formed of adhesive. Heat and pressure of a heat-sealing die or other mechanism are applied to the layered material around the perimeter of the entire lancet to form a heat seal line. As the heat and pressure are applied to the layered material, the adhesive in the intermediate layer seeps through the inner and outer walls along the heat seal line to secure the walls together. To use the lancet, a user must peel apart the two walls along the heat seal line to expose the lancet. One issue often associated with such packaging is that the user must separate the walls while at the same time maintain the lancet in the sterile package until the lancet is ready to be used. Another difficulty that can be associated with such packaging is an excess amount of adhesive may seep through the inner and outer walls making it more difficult for a user to separate the walls.

Another form of packaging the lancet in a sterile environment involves covering the tip of the lancet with a protective cap. One form of applying a protective cap onto the tip of the lancet is by injection molding. A material, usually plastic, is heated until it can flow and then the material is injected into a mold that contains a lancet. The mold is shaped to form a protective cap to cover the lancet. The material usually remains in the mold until it has cooled and solidified. The protective cap and lancet are removed from the mold.

A potential drawback for either sealing an entire lancet between two walls of material or injection molding is a long cycle time in which to seal the lancet or form the cap. An example cycle time to seal an entire lancet between two walls of a material would include placing the entire lancet between two walls of a layered material and heat sealing a portion of the layered material around the entire lancet. An example cycle time for injection molding would include heating the material, injecting the heated material into a mold, cooling the material in the mold to form a protective cap, and removing the cap and lancet from the mold. Another potential difficulty with sealing an entire lancet between two walls of material or injection molding is that both forms tend to be more costly to manufacture to protect the sterility of the lancet when compared to other forms of maintaining the sterility of the lancet. Another obstacle often associated with a lancet is the safe disposal of the lancet upon use of the lancet. For example, the user or medical practitioner using the lancet would not want to accidentally prick another person or themselves with a contaminated lancet thereby potentially exposing this person or themselves to disease. Frequently, the two walls of the sealed packaged lancet are separated to expose the lancet however; the two walls usually cannot be resealed together by the medical practitioner or the patient for safe disposal of a used lancet. Similarly, the replacement of the injection molded cap onto the lancet tip may be difficult for persons with limited hand dexterity.

Maintaining the sterility of the lancet while at the same time providing for ease in removal of the protective cap can be difficult, especially when the test is self-administered. Usually, the subject is either elderly or otherwise has some infirmity that reduces their hand dexterity, which in turn makes removal of the cap difficult. One solution has been to weaken the connection between the cap and the lancet, but by weakening this connection, the protective caps are more prone to be dislodged during shipping.

Thus, there remains the need for further improvement in this field.

SUMMARY

One aspect of the present invention concerns a method for covering a lancing tip. At least the lancing tip is sandwiched between a first web of material resistant to melting at a specific temperature and a second web of material meltable at the specific temperature. The method also includes melting the second web by heating both the first web and the second web to the specific temperature in order to encapsulate at least the lancing tip in a sterile enclosure. Further, during the melting the first web remains in an unmelted state to form a ribbon that protects the integrity of the lancing tip.

Another aspect concerns a device for maintaining sterility and protecting integrity of a lancet tip. The device includes a lancet with a lancet tip for forming an incision in skin. Further, a first web of a multi-layered material contacts the lancet tip. A second web of the multi-layered material contacts the first web and sandwiches the lancet tip between the first web and the second web to protect the sterility of the lancet tip. A structure is formed by heat fusing together the first web and the second web to protect the integrity of the lancet tip. Further, the structure is cut to form a protective cap that covers the lancet tip.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
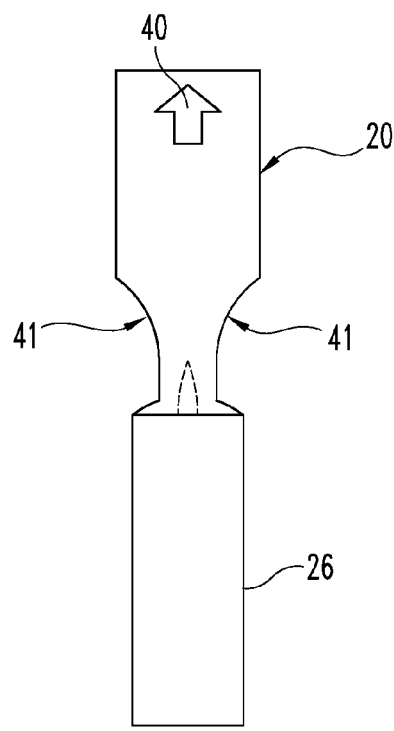
FIG. 1 is a front view of a protective cap covering a lancet according to one embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The present invention generally concerns a protective cap that protects the integrity and sterility of a lancet tip for a lancet and/or an integrated lancing test strip. It is envisioned that other devices may be protected with the protective cap. One technique that quickly manufactures the protective cap is to sandwich a lancet tip between two webs of a multi-layer material to protect the sterility of the lancet tip, heat seal the webs together to form a structure to protect the integrity of the lancet tips, and cut the structure to form the protective cap that covers the lancet tip. In another technique, a plurality of lancet tips are sandwiched between the two webs of the multi-layer material and a plurality of protective caps are formed from the structure. The layers of material for the webs are chosen based on the application and desired properties or characteristics of the layers to protect the integrity and sterility of the lancet tip. The layers of material in contact with a lancet tip have a low melting point that enables the layers to melt quickly and encapsulate the lancet tip as heat energy is applied to the web. The sterility of the lancet tip is protected with encapsulation of the lancet tip. Further, a high melting point for the layers of webs that form the exterior of the cap will not melt as heat energy is applied to the multi-layered material. These exterior layers of web perform like a shell or mold as heat energy is applied to the webs during the manufacturing process. Since these exterior layers do not melt, heat energy can be applied to the exterior layers and the inner layers thus melting the inner layers and encapsulating the lancet tip. Strong cohesive layers of the webs positioned to form exterior surfaces of the cap also provide a rigid protective outer layer or shell to protect the integrity of the lancet tip.

Selected features from different embodiments of the present invention will be described with reference to a bare lancet or an integrated lancing test strip of the type illustrated in the drawings, but it should nevertheless be appreciated that these features can be incorporated into other types of designs. As a non-limiting example, although the illustrated integrated lancing test strips have a lancet that is fixed relative to the rest of the test strip, it should be appreciated that the lancet or other portions of the test strip can be moveable relative to the rest of the test strip. It is envisioned that multiple lancets with protective caps or multiple integrated lancing test strips with protective caps can be stored or joined together in a container to form a magazine or cassette.

A protective cap 20 according to one embodiment of the present invention, will now be described with reference to FIGS. 1, 2, and 3. The protective cap 20 includes a first web 22 and a second web 24. A lancet 26 is sandwiched between the first web 22 and the second web 24. As illustrated in FIG. 3, the first web 22 and the second web 24 are made of a multi-layer material 28. In the embodiment shown in FIG. 3, the multi-layer material 28 is formed from a first layer 30 and a second layer 32. In other embodiments, the multi-layer material 28 may have additional layers other than first layer 30 and second layer 32 or may have only a single layer. In yet another embodiment, a portion of the first web 22 and/or the second web 24 melts at a specific temperature to encapsulate at least a lancet tip of lancet 26. In this embodiment, another portion of the first web 22 and/or the second web 24 does not melt at the same specific temperature however this portion forms a rigid outer layer of the protective cap 20 to protect the integrity of the lancet tip. As a non-limiting example, the first web 22 and the second web 24 can be made of polystyrene and polyethylene.

In the illustrated embodiment, lancet 26 has a substantially flat shape. Lancet 26 with a flat shape is manufactured easily and quickly, and multiple lancets 26 having flat shapes can be easily stacked or stored in a cassette or magazine. As should be appreciated, the lancet 26 can be various geometric shapes. For example, lancet 26 can be rounded. Lancet 26 can be made from various materials, such as metal, plastic, ceramic, or a combination of metals such as metal and plastic to name a few materials.

Figure 4:
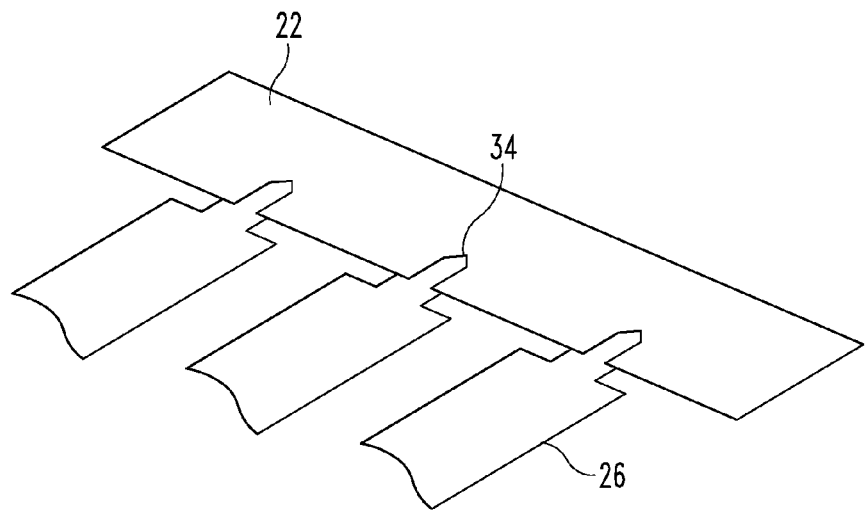
FIG. 4 is a perspective view of a plurality of lancets on top of a web during one stage of a manufacturing process.

As shown in FIG. 4, the lancet 26 has a lancet tip 34. The lancet tip 34 is substantially triangular in shape, however it should be appreciated that the lancet tip 34 can be various geometric shapes. The lancet tip 34 is configured to cut an incision into skin or other types of tissues.

Figure 2:
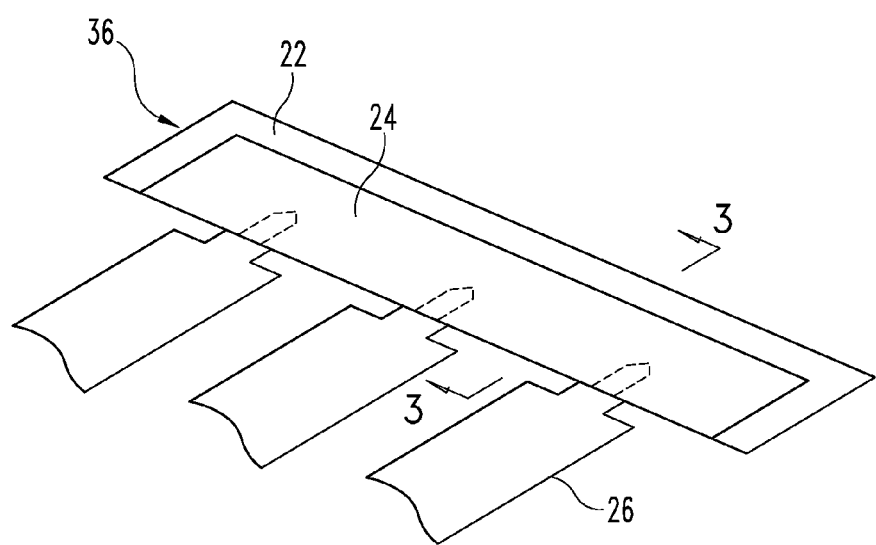
FIG. 2 is a perspective view of a plurality of lancets sandwiched between two webs according to the embodiment shown in FIG. 1.
Figure 3:
FIG. 3 is a partial cross sectional view of the FIG. 2 webs as taken along line 3-3 in FIG. 2.

As shown in FIG. 2, the protective cap 20 is formed from the first web 22 and the second web 24. The first web 22 and the second web 24 are shown as rectangular pieces of multi-layer material 28 however in other embodiments the first web 22 and the second web 24 may be shaped differently. It should be appreciated that first web 22 and/or second web 24 shaped as rectangular pieces tend to roll onto a spindle uniformly as compared to other shapes. It is envisioned that a spindle of first web 22 and a spindle of second web 24 may be used to form the protective cap 20 to increase the speed of manufacturing the protective cap 20 as discussed below. For illustrative purposes, in FIG. 2 the first web 22 has a width greater than a width of the second web 24. In other forms, the width of the first web 22 may be substantially equal to or less than the width of the second web 24. In addition, for illustrative purposes, the length of the first web 22 is greater than the length of the second web 24 in FIG. 2. As should be appreciated in other forms the length of the first web 22 may be substantially equal to or less than the length of the second web 24.

Multi-layer material 28, as shown in FIG. 3, includes first layer 30 and second layer 32. In one embodiment, multi-layer material 28 can be formed by co-extruding first layer 30 and second layer 32 from a device onto a surface configured to receive first layer 30 and second layer 32. It is envisioned that the surface is shaped to receive first layer 30 and/or second layer 32 to form multi-layer material 28, however multi-layer material 28 can be removed from the surface. In another form, first layer 30 may be extruded from a device onto a surface and second layer 32 may be extruded onto first layer 30 to form the multi-layer material 28. It should be appreciated that multi-layer material 28 can be formed by other techniques. It is envisioned that multi-layer material 28 can be bent or rolled onto a spindle for storage and/or use during the manufacture of the protective cap 20.

The materials for first layer 30 and second layer 32 are chosen based on desired characteristics or properties of the protective cap 20. One desirable characteristic is a high melting point of the first layer 30. First layer 30 of first web 22 and first layer 30 of second web 24 form an exterior surface of the protective cap 20 as shown in FIGS. 1, 2, and 3. A high melting point for first layer 30 prevents first layer 30 from melting as heat energy is applied to web 22 and/or web 24 to heat the webs to a specific temperature. As heat energy is applied to web 22 and/or web 24, first layer 30 performs similar to a shell or mold for the second layer 32 during the manufacturing process. Another desired characteristic is a low melting point of second layer 32. For example, second layer 32 of first web 22 and second layer 32 of second web 24 contact lancet tip 34 in the embodiment shown in FIGS. 1, 2, and 3. A low melting point for second layer 32 enables second layer 32 to melt quickly and encapsulate lancet tip 34 with a small amount of heat energy applied to it to heat second layer 32 to the specific temperature. Heat energy can be applied to first layer 30 and second layer 32 in contact with the lancet tip 34 thus melting second layer 32 and encapsulating the lancet tip 34. Encapsulating the lancet tip 34 with the second layer 32 protects the sterility of the lancet tip 34. A low melting point decreases the amount of time required to heat the second layer 32. Another desirable property is the cohesiveness of first layer 30 and/or second layer 32. In the embodiment shown in FIGS. 1, 2, and 3, first layer 30 of first web 22 and first layer 30 of second web 24 each form an exterior surface of the protective cap 20. A strong cohesive first layer 30 of first web 22 and first layer 30 of second web 24 provide a rigid protective outer layer or shell to protect the integrity of lancet tip 34. An additional desirable property or characteristic is the adhesiveness of first layer 30 to second layer 32. The adhesiveness of first layer 30 to second layer 32 enables the layers to stick together to form the multi-layer material 28. It should be appreciated that an intermediate layer of adhesive can be placed between the first layer 30 and second layer 32 to hold these layers together. Other characteristics as desired can be chosen to determine the type of material to be used for the first layer 30 and/or the second layer 32.

In one form wherein heat energy from a laser is applied to web 24, the first layer 30 and/or second layer 32 of web 22 may be colored a dark color to absorb heat energy from the laser. In this form, energy from a laser is applied to the first layer 30 of web 24. The first layer 30 and the second layer 32 of web 24 are colorless to enable the darkly colored web 22 to absorb heat energy from the laser. As should be appreciated, other forms of applying heat energy to web 22 and/or web 24 are discussed below. It is envisioned that first layer 30 and/or second layer 32 of web 22 and web 24 may be any color the user desires if heat energy in forms other than a laser are applied to web 24.

In one form, the first layer 30 and/or the second layer 32 may have a smooth surface for receiving the lancet tip 34 and/or a user or device, respectively. In another form, second layer 32 has ridges or a texture on its surface that contacts the lancet tip 34. Further, when heat energy is applied to the web 22 and/or web 24, the ridges enable the second layer 32 to melt quickly and encapsulate the lancet tip 34.

First layer 30 and second layer 32 can be made from various materials. In one embodiment, first layer 30 is made of polystyrene and second layer 32 is made of polyethylene. By non-limiting example, first layer 30 is approximately 0.3 millimeters and second layer 32 is approximately 0.1 millimeters. As should be appreciated in this embodiment, first layer 30 of first web 22 is positioned away from lancet tip 34 and forms a rigid outer layer of the protective cap 20. As should also be appreciated in this embodiment, heating the second layer 32 positioned adjacent the lancet tip 34 encapsulates the lancet tip 34 within the second layer 32. In other embodiments, first layer 30 may be formed by materials such as metal, plastic, or polyester, or composites such as metal and plastic, or any other materials in which the first layer 30 is a heat resistant material that also forms a protective outer layer of the cap 20. Second layer 32 may be formed by materials such as thermoplastic, polymer, plastic, or any other materials that can melt to encapsulate lancet tip 34 and can be removed from lancet tip 34 for use of the lancet 26.

Lancet tip 34 is sandwiched between first web 22 and second web 24. As shown in FIG. 2, multiple lancets 26 can be sandwiched between first web 22 and second web 24. In this form, first web 22, lancets 26, and second web 24 are assembled in a layer like fashion such that multiple protective caps 20 can be easily assembled and manufactured in a continuous fashion. In one manufacturing process, as shown in FIG. 4, a continuous web 22 is positioned such that multiple lancet tips 34 are placed in a side-by-side fashion on top of web 22. Next, as shown in FIG. 2, a continuous web 24 is placed over the lancet tips 34 thereby sandwiching the lancet tips 34 between the first web 22 and the second web 24. As discussed below, heat energy is applied to the web 22 and/or the web 24. It is envisioned that various techniques may be used to sandwich the lancet tips 34 between the first web 22 and the second web 24 and increase the speed of manufacturing the protective caps 20. By way of non-limiting example, first web 22 can be rolled onto a first spindle and second web 24 can be rolled onto a second spindle to increase the speed of manufacturing. Further, as the first web 22 and the second web 24 are unrolled, a plurality of lancet tips 34 are positioned in a side-by-side fashion between the first web 22 and the second web 24. In this form, a thermoplate can apply heat energy to the second web 24 as web 24 is unrolled from the spindle. The heated web 24 is placed on top of the first web 22 wherein second layer 32 of web 22 and second layer 32 of web 24 melt to encapsulate the lancet tip 34.

Figure 5:
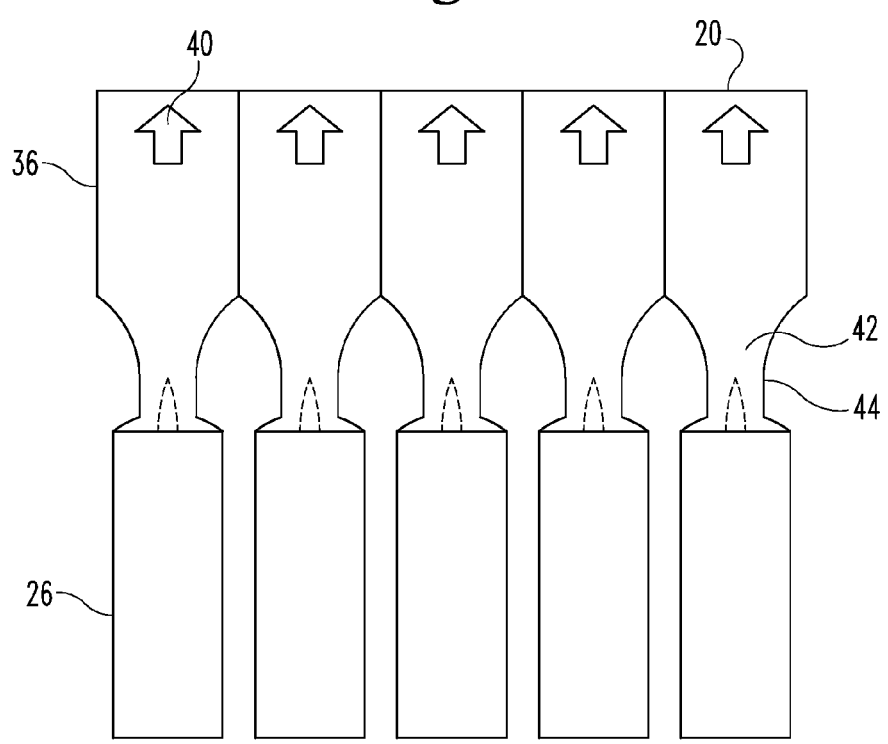
FIG. 5 is a front view of a plurality of protective caps covering a plurality of lancet tips of lancets, each cap has a rectangular shape with a tapered end having edges concave in shape.

First web 22 and second web 24 are heat fused together to create a structure or one-piece ribbon 36 as shown in FIG. 5. Heat energy is applied to first web 22 and/or second web 24 to bond the webs together to form the structure 36 to protect the integrity of the lancet tip 34. The lancet tip 34 remains sandwiched between the webs while heat energy is applied to first web 22 and/or second web 24. The lancet tip 34 is embedded in the structure 36 as the second layer 32 of first web 22 and/or the second layer 32 of second web 24 melts and encapsulates the lancet tip 34. One source of heat energy is the application of electromagnetic radiation by a laser to the first web 22 and/or the second web 24. For the application of heat energy by a laser to second web 24, it is beneficial to have a darkly colored first web 22 and a colorless second web 24 as the laser emits radiation toward the colorless second web 24. The darkly colored first web 22 absorbs more heat and energy from the laser thus heating and melting the second layer 32 of the first web 22 and the second layer 32 of the second web 24. In one embodiment, a laser with electromagnetic radiation produced with an approximate wavelength of 790 to 830 nanometers may be used as a source of heat energy. Another example of heat energy can be infrared radiation applied to first web 22 and/or second web 24 to form structure 36. Thermal plates or thermal rollers may also be applied to the first web 22 and/or the second web 24 to form structure 36. One range of heat for the thermal plates or thermal rollers may be approximately 95° to 130° Celsius. In one form, the structure 36 is cooled to a desired temperature to form the protective cap 20 to cover the lancet tip 34.

Figure 10:
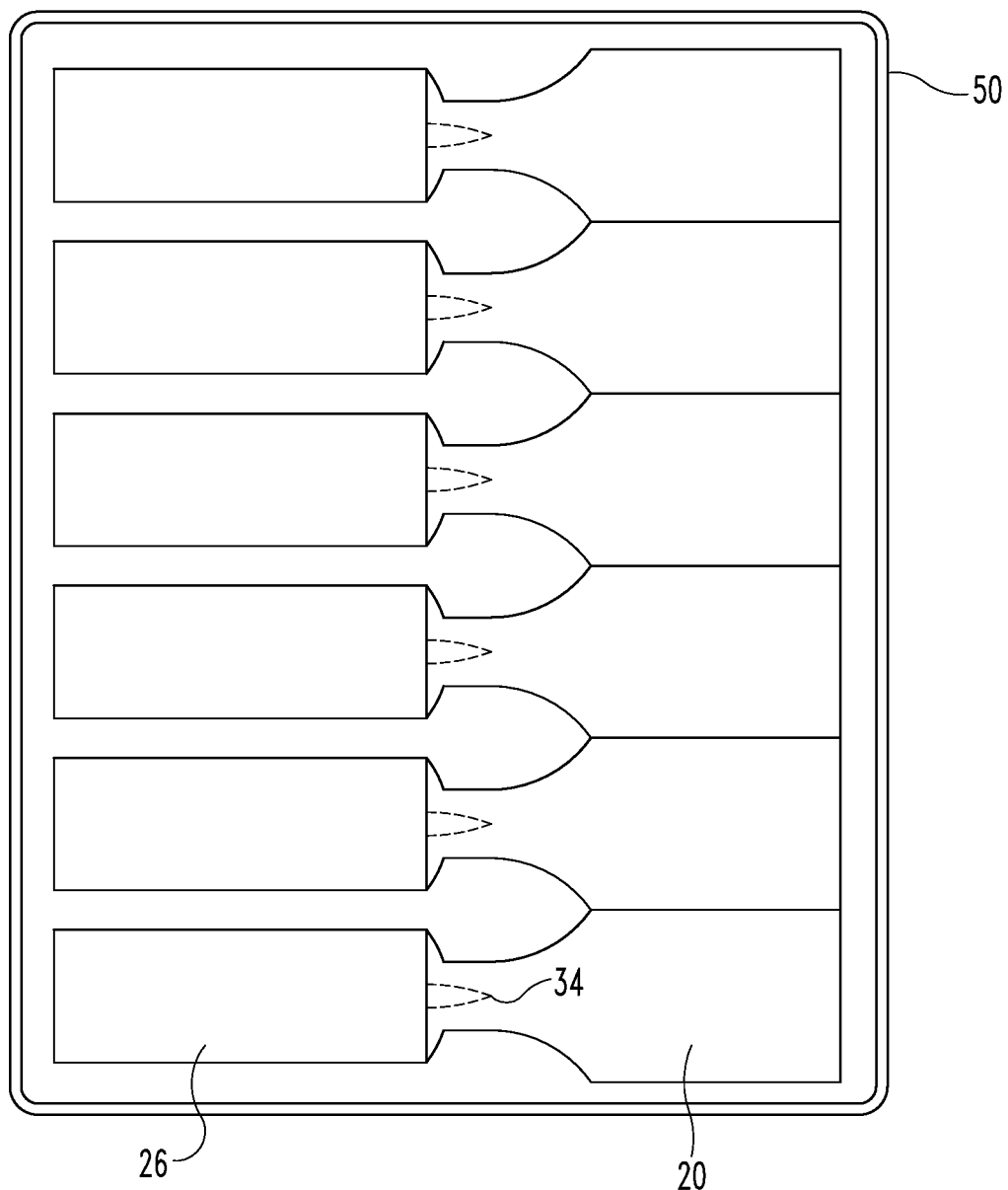
FIG. 10 is a front cross-sectional view of a plurality of protective caps covering a plurality of lancet tips of lancets in a cartridge or container.

One-piece structure 36 can be cut into a desired shape to form a pull-off tab or protective cap 20. A few shapes for the cap 20 are rectangular, circular, or triangular. The shape of cap 20 can vary whether the cap 20 covers a lancet 26 or an integrated lancing test strip 38. Further, the shape of cap 20 can vary whether it is for use with an individual use device or with a cartridge or cassette 50 that stores multiple lancets 26 or integrated lancing test strips 38 as illustrated in FIG. 10 and described below. The cartridge 50 can be configured to store multiple lancets 26 or integrated lancing test strips 38 with caps 20. In another form, one-piece structure 36 is not cut but remains a continuous strip. In this embodiment, the structure 36 forms a continuous strip that can be received in a cartridge or magazine. Various techniques may be used to cut the structure 36. One form of cutting the structure 36 to form the protective cap 20 is die cutting. Another technique used to cut structure 36 is to punch structure 36 with a machine that forms the shape of each protective cap 20. Yet another technique used to cut structure 36 to shape the protective cap 20 is a rotary shear.

Figure 8:
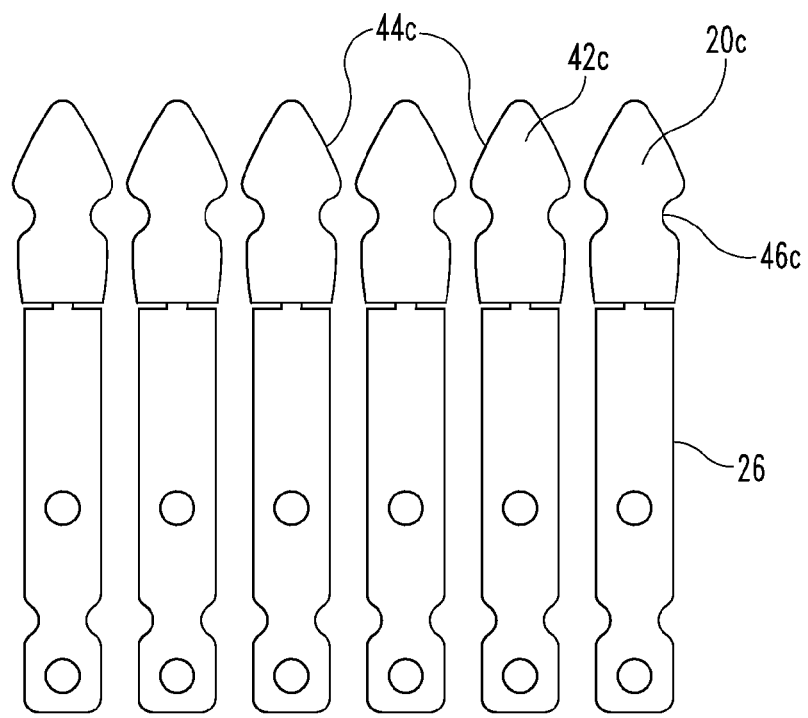
FIG. 8 is a front view of a plurality of protective caps covering a plurality of lancet tips of lancets, each cap has a rectangular shape with a tapered end having edges triangular in shape.
Figure 9:
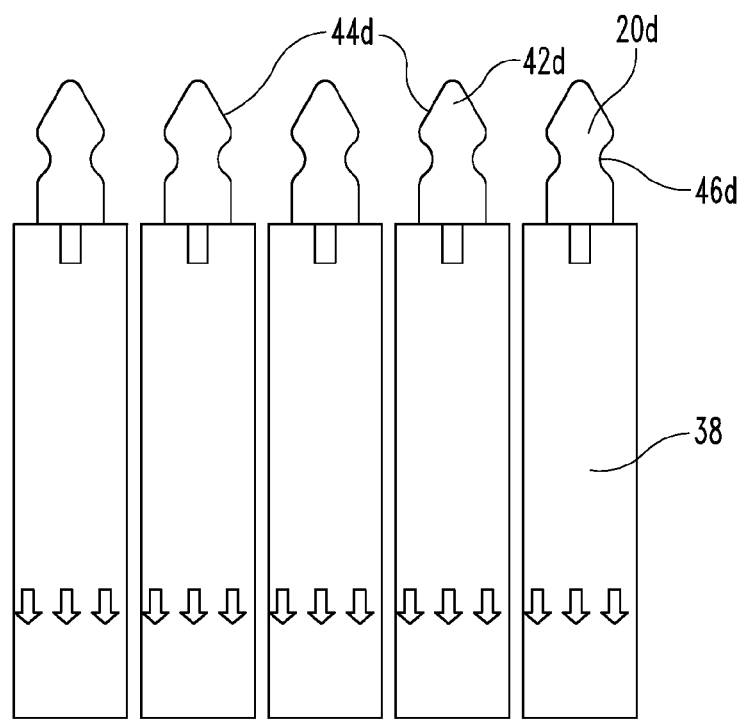
FIG. 9 is a front view of a plurality of protective caps covering a plurality of lancet tips of integrated lancing test strips, each cap has a rectangular shape with a tapered end having edges triangular in shape.

The protective cap 20 protects the integrity and sterility of the lancet tip 34. As should be appreciated, the protective cap 20 can also protect the integrity and sterility of an integrated lancing test strip 38 as shown in FIGS. 8 and 9. As should also be appreciated, the integrated lancing test strip 38 includes a lancet and a test strip or other testing means to analyze bodily fluid. The test strip can analyze fluid through electrochemical means, such as electrodes and a reagent, optical, and/or magnetic analysis to name a few means. In one embodiment, the lancet is sterilized before attaching the lancet to the test strip to form the integrated lancing test strip 38. In another embodiment, the lancet is attached to the test strip to form the integrated lancing test strip 38 and then the lancet is sterilized. In this embodiment, the test strip is calibrated.

To use the lancet 26, the cap 20 must be removed from the lancet tip 34. To remove the cap 20 and expose the lancet tip 34 for an individual use device, a user pulls the cap 20 in a direction opposite to the lancet 26. The cap 20 functions as a pull-off tab in which the user removes the cap 20 by pulling the cap 20 in a direction away from the lancet 26. To aid a user in removing the cap 20, an indicator or symbol 40 may be placed on the cap 20 as shown in FIG. 5. As shown, the symbol 40 aids the user by giving instructions or showing the direction in which to pull the cap 20 to remove it from the lancet tip 34. In other forms, the symbol 40 may be a manufacturer's logo, trademark, or any other words or figures. To manually remove the cap 20, a user grabs the cap 20 in areas marked by arrows 41 as shown in FIG. 1. The user begins to pull the cap 20 in a direction away from the lancet 26 as indicated by the symbol 40 in FIG. 5. As the user exerts a force on the cap 20, the molded cap 20 shears away from the lancet tip 34. As the user continues to pull the cap 20 away from the lancet 26, the cap 20 eventually breaks its seal with the lancet tip 34, and the cap 20 is fully removed from the lancet 26 to expose the lancet tip 34.

In some forms, the cap 20 and the lancet tip 34 are stored in a cassette or cartridge, and to remove the cap 20 from the lancet tip 34 a tool within the integrated testing device will engage the cap 20 and remove it to expose the lancet tip 34. It should be appreciated there are various techniques for automatically removing the cap 20 from the lancet 26 or the integrated lancing test strip 38 housed in a cassette. These techniques are known in the art and not important to appreciate the present invention, therefore these techniques will not be discussed in detail below.

Figure 6:
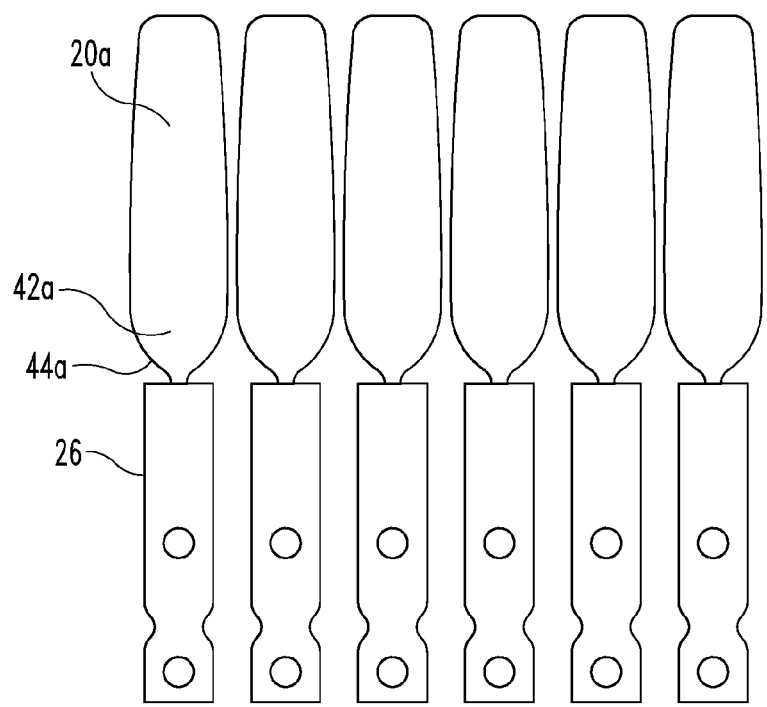
FIG. 6 is a front view of a plurality of protective caps covering a plurality of lancet tips of lancets, each cap has a rectangular shape with a tapered end having edges convex in shape.
Figure 7:
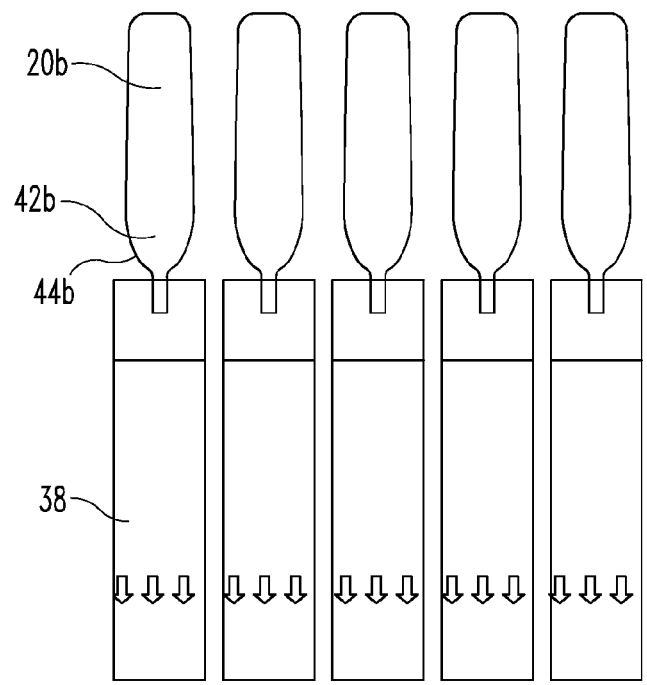
FIG. 7 is a front view of a plurality of protective caps covering a plurality of lancet tips of integrated lancing test strips, each cap has a rectangular shape with a tapered end having edges convex in shape.

As illustrated in FIGS. 5, 6, 7, 8, and 9 and described below, the structure 36 may be cut to form multiple protective caps 20 with various shapes. As should be appreciated, the shaped protective caps 20 illustrated in FIGS. 5, 6, and 7 are configured for use with an individual use testing device in which the user will manually remove the cap 20 from the lancet tip 34. As should also be appreciated, the shaped protective caps 20 illustrated in FIGS. 8 and 9 are configured for use with an integrated testing device that stores a plurality of protective caps 20 and lancets 26 (or integrated lancing test strips 38) in a cassette.

As illustrated in FIG. 5, the structure 36 may be cut to form an ergonomically shaped protective cap 20. The protective cap 20 has a tapered end 42. Protective cap 20 is substantially rectangular in shape. As should be appreciated, tapered end 42 can be shaped to aid the user in grasping and removing the protective cap 20. Tapered end 42 has edges 44 that are semicircular in shape. In addition, edges 44 are concave in shape.

In accordance with FIG. 6, protective cap 20a, includes tapered end 42a. As should be appreciated, protective cap 20a is similar to cap 20. Tapered end 42a includes edges 44a that are circular in shape however; the edges 44a form a convex shape.

Referring to FIG. 7, protective cap 20b has a tapered end 42b with edges 44b. Protective cap 20b is similar to cap 20a.

With reference to FIG. 8, protective cap 20c is substantially rectangular in shape with a tapered end 42c having a triangular shaped edge 44c in the form of an isosceles triangle. In other forms, the shaped edge 44c can be angled differently. For example, the shaped edge 44c can form a right triangle, or a scalene triangle, to name a few shapes. Protective cap 20c also has indentations 46c. Indentations 46c are semicircular in shape. In other forms, the indentations 46c can be shaped differently. As should be appreciated, the shaped edge 44c and/or the indentations 46c assist a device, mechanical or electrical, in grasping and removing the protective cap 20c.

A protective cap 20d according to another form is illustrated in FIG. 9. As shown, the protective cap 20d has a tapered end 42d. Tapered end 42d includes triangular shaped edges 44d in the form of an isosceles triangle. As should be appreciated, protective cap 20d is similar to protective cap 20c.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device, comprising:
a lancet having a lancet tip configured to form an incision in skin;
a first web of a multi-layered material, wherein the multi-layered material has a heat-resistant first layer and a heat-sensitive second layer;
a second web of the multi-layered material, the second layer of the second web contacting the second layer of the first web and sandwiching the lancet tip between the first web and the second web to protect sterility of the lancet tip;
wherein the second layer of the first web and the second layer of the second web are configured to melt together to form a cap to encapsulate the lancet tip in the melted second layers of the first and second webs; and
wherein the first layer of the first web and the first layer of the second web form a protective outer surface of the cap, wherein the cap is adapted to be removed from the lancet.

2. The device of claim 1, wherein:
the first layer includes polystyrene; and the second layer includes polyethylene.

3. The device of claim 1, further comprising:
a plurality of the lancet tips sandwiched between the first web and the second web.

4. The device of claim 1, further comprising:
a plurality of the lancet tips sandwiched between the first web and the second web;
a plurality of the caps configured to encapsulate said plurality of the lancet tips, wherein a single cap is associated with a single lancet tip; and
a cartridge for storing the plurality of the caps and the plurality of the lancet tips.

5. The device of claim 1, wherein the cap cut to cover the lancet tip.

6. The device of claim 1, further comprising:
a test strip attached to the lancet and adapted to analyze bodily fluid from the incision.

7. The device of claim 1, further comprising:
an adhesive layer positioned between the heat-resistant first layer and the heat-sensitive second layer to hold the first and second layers together.

8. The device of claim 1, wherein the first layers of the first and second webs are made of a transparent material and the second layers of the first and second webs are made of an opaque material.

9. The device of claim 1, wherein at least one of the second layer of the first web and the second layer of the second web includes a plurality of ridges that are configured to melt together to encapsulate the lancet tip.

10. The device of claim 1, wherein the second layers of the first and the second webs have a lower melting temperature point than the first layers of the first and the second webs.

11. The device of claim 1, wherein the first layers of the first and the second webs are configured to contain the melted second layers of the first and the second webs.

12. A device, comprising:
a lancet having a lancet tip configured to form an incision in skin;
a cap including a first web and a second web of a multi-layered material, wherein the multi-layered material has a heat-resistant first layer and a heat-sensitive second layer,
the second layer of the second web configured to contact the second layer of the first web and to sandwich the lancet tip between the first web and the second web to protect sterility of the lancet tip; and
wherein the second layer of the first web and the second layer of the second web are configured to melt together to form the cap to encapsulate the lancet tip in the melted second layers, wherein the cap is adapted for removal from the lancet tip.

13. The device of claim 12, further comprising:
a test strip attached to the lancet and adapted to analyze bodily fluid from the incision.

14. The device of claim 12, wherein the second layers of the first and the second webs each include a plurality of ridges that are configured to melt together to encapsulate the lancet tips.

15. The device of claim 12, wherein the first layers of the first and the second webs form a mold to contain the melted portions of the second layers of the first and the second webs.

16. A device, comprising:
a lancet having a lancet tip configured to form an incision in skin;
a cap configured to cover the lancet tip, the cap having a first web and a second web of a multi-layered material, the multi-layered material including a heat-resistant layer and a heat-sensitive layer, the heat-sensitive layer of the first web is configured to contact the heat-sensitive layer of the second web; and
the heat-sensitive layers of the first and second webs are configured to melt together to sandwich the lancet tip in the melted layers and form the cap.

17. The device of claim 16, further comprising:
a plurality of lancet tips sandwiched between the first web and the second web.

18. The device of claim 17, further comprising:
a plurality of caps configured to cover the plurality of lancet tips; and
a cartridge configured to store the plurality of lancets and the plurality of caps.

19. The device of claim 16, further comprising:
a test strip attached to the lancet and adapted to analyze bodily fluid from the incision.

* * * * *